United States Patent
Murphy

(10) Patent No.: US 6,273,916 B1
(45) Date of Patent: Aug. 14, 2001

(54) METHOD AND APPARATUS FOR STRENGTHENING VERTEBRAL BODIES

(75) Inventor: Kieran Murphy, Baltimore, MD (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/425,480

(22) Filed: Oct. 22, 1999

(51) Int. Cl.[7] .................................................. A61F 2/36
(52) U.S. Cl. ........................................................ 623/23.62
(58) Field of Search ........................... 623/23.62; 606/63, 606/86, 92, 93; 424/422, 423, 501

(56) References Cited

U.S. PATENT DOCUMENTS

| | | | |
|---|---|---|---|
| 4,843,112 | * 6/1989 | Gerhart et al. | 523/114 |
| 4,973,168 | * 11/1990 | Chan | 366/139 |
| 5,512,610 | * 4/1996 | Lin | 523/116 |

(List continued on next page.)

FOREIGN PATENT DOCUMENTS

9918894 * 4/1999 (WO) .................................. 623/23.62

OTHER PUBLICATIONS

International Radiologic Procedures with CT Guidance in Cancer Pain Management Afshin Gangi, MD et al.; Scientific Exhibit, vol. 16, No. 6, pp. 1289–1306.

Spinal Metastases; Indications for and Results of Percutaneous Injection of Acrylic Surgical Cement; Alain Weill, M.D et al.;Radiology; vol. 199, No.1, pp. 241–247.

Percutaneous Vertebroplasty Guided by a Combination of CT and Fluoroscopy; Afshin Gangi et al.; American Journal of Neuroradiology; vol.15, Jan. 1994; pp. 83–86.

Percutaneous Polymethylmethacrylate Vertebroplasty in the Treatment of Osteoporotic Vertebral body Compression Fractures: Technical Aspects; Mary E. Jensen et al.; American Journal of Neuroradiology; vol. 18, Nov., 197; pp. 1897–1904.

Percutaneous Vertebroplasty for Osteolytic Metastases and Myeloma: Effects of the Percentage of Lesion Filling and the Leakage of Methyl Methacrylate at Clinical Follow–up; Anne Cotten, M.D. et al.; Radiology; Aug., 1996; pp. 525–530.

(List continued on next page.)

Primary Examiner—Jeffrey A. Smith
Assistant Examiner—Eduardo C. Robert
(74) Attorney, Agent, or Firm—Anton P. Ness

(57) ABSTRACT

An apparatus and method for performing vertebroplasty are provided. In one embodiment of the invention, there is provided a kit for performing vertebroplasty having two packs, each pack having the necessary components for performing vertebroplasty via each pedicle of the damaged vertebrae. Each pack is sterilized, so that if the vertebroplasty performed via one pedicle is sufficient, then the second pack can be saved for later used. In another embodiment, each pack within the kit has two cements, each cement having different imaging properties, such that each cement will appear different when viewed with an imaging device in the lateral plane and/or will be viewable when overlapping. A presently preferred embodiment involves two packs having methylmethacrylate powder but each pack has a different amount of opacifier, either as supplied or added by the vertebroplasty professional, such that when each cement is mixed and injected, each cement is visible when exposed to X-ray lateral fluoroscopy. A method is also provided that utilizes the kit, and which allows a medical professional to monitor a second injection of cement via the second pedicle and thus reduce the risk of spinal cord compression or venous filling due to unwanted flow of cement into the spinal canal.

20 Claims, 9 Drawing Sheets

U.S. PATENT DOCUMENTS 5,586,821 * 12/1996 Bonitati et al. .................. 366/136
6,020,396 * 1/2000 Jacobs .............................. 523/116
6,040,408 * 3/2000 Koole ............................... 526/292.1

OTHER PUBLICATIONS

Percutaneous Vertebroplasty: Indications, Technique, and Complications; C. Depriester et al.; Interventional Neuroadiology, conners & Wojak, W.B. Saunder Publ., 1999; Chapter 29, Chapter 29, pp. 346–356.

Percutaneous Vertebroplasty with Polymethylmethacrylate; Technique, Indications, and Results; Hervé Deramond, M.D. et al.; Interventional Procedures in Musculoskeletal Radiology; vol. 36, No. 4, May, 1998; p. 533–546.

Percutaneous Vertebroplasty: State of the Art; Anne Cotten, M.D. et al; Scientific Exhibit, vol. 18, No. 2, Mar.–Apr. 1998; pp. 311–323.

* cited by examiner

METHOD AND APPARATUS FOR STRENGTHENING VERTEBRAL BODIES

FIELD OF THE INVENTION

The present invention relates to vertebroplasty and a method and apparatus for strengthening vertebral bodies.

BACKGROUND OF THE INVENTION

Percutaneous vertebroplasty is a well-known procedure involving the injection of a bone cement or suitable biomaterial into a vertebral body via percutaneous route under X-ray guidance, typically lateral projection fluoroscopy. The cement is injected as a semi-liquid substance through a needle that has been passed into the vertebral body, generally along a transpedicular or posterolateral approach. The three main indications are benign osteoporotic fractures, malignant metastatic disease and benign tumours of the bone.

Percutaneous vertebroplasty is intended to provide structural reinforcement of a vertebral body through injection, by a minimally invasive percutaneous approach, of bone cement into the vertebral body. See, for example, Cotton A., et al "Percutaneous vertebroplasty: State of the Art." *Radiograhics* 1998 March–April; 18(2):311–20; discussion at 320–3. Percutaneous vertebroplasty can result in increased structural integrity, decreased micromotion at the fracture site, and possibly a destruction of pain fibres due to the heat of the bone cement as it polymerizes and sets. Complete pain relief can be achieved in up to eighty percent of patients. As known to those of skill in the art, the cement should have properties that, when injected, can increase vertebral body stiffness and compressive strength. It is generally preferred that the cement is liquid enough to flow into fracture planes and to fuse them. There is some debate about the appropriate thermal properties, but it is believed by some that the heating effect can be beneficial and cause death to local nerve endings involved in pain stimulation. It is generally accepted that most pain relief is achieved due to increased structural integrity.

The general steps for performing a vertebroplasty are as follows. The patient is placed in the prone position and the skin overlying the fractured vertebrae is prepped and draped. A suitable local anaesthetic such as 1% Lidocaine is injected into the skin underlying fat and into the periosteum of the pedicle to be entered. Next, a skin incision of about five millimetres is made with a No. 11 scalpel blade or other suitable surgical implement. The decision regarding which pedicle to use is made based on CT (computed tomography) and MR (magnetic resonance) images. A needle of an appropriate gauge (such as eleven gauge or thirteen gauge in a smaller vertebral body) is passed down the pedicle until it enters the vertebral body and reaches the junction of the anterior and middle thirds. This area is the region of maximum mechanical moment and usually the area of greatest compression. At this point a vertebrogram can be performed, if desired, by the injection of non-ionic X-ray contrast into the vertebral body to look for epidural draining veins.

Next, a cement is prepared. One suitable cement is a mixture of barium powder with methyl methacrylate powder and with a monomer liquid added to the mixture. Known cement products include Howmedica Simplex from Stryker Corporation 6300 Sprinkle Road, Kalamazoo, Mich. 49001, Osteobond from Zimmer Inc., 1800 West Center Street, Warsaw Ind. 46580, and Codman Cranioplastic from Codman, A Johnson & Johnson Company, 325 Paramount Drive, Raynham, Mass. 02767. From the moment that the monomer liquid is added to the powder there are generally about four to eleven minutes, with an average of about five to six minutes, before the cement thickens and becomes unworkable. Cement is inject under lateral X-Ray projection fluoroscopy imaging. The posterior aspect of the vertebral body is an important area to observe for posterior extension of cement, and it is generally accepted that this should be watched constantly during the injection. The injection is stopped as the cement starts to extend into some unwanted location such as the disc space or towards the posterior quarter of the vertebral body, where the risk of epidural venous filling and hence spinal cord compression is greatest. The injection is also discontinued if adequate vertebral filling is achieved. On average, about four to five cubic-centimetres of cement can be injected on each side, and it is known to inject up to about eight to nine cubic-centimetres per side.

About forty percent of the time it is possible to adequately fill a vertebral body from a single injection. It the vertebral body is not adequately filled during the first injection, it is necessary to pass a second needle down the other pedicle and inject more cement. The second side is anaesthetized, and a second skin incision is made. A second needle is passed down the other pedicle and advanced into the vertebral body to the junction of the anterior and middle third of the vertebral body. Again, cement is mixed and injected under lateral projection fluoroscopy imaging.

However, as is known to those of skill in the art, it can be very difficult to visualize the injection of cement against the existing cement from the first injection. Under the lateral projection fluoroscopy imaging, the second injection is visualized as a gradual subtle increase in the overall density or when the cement therefrom flows beyond the boundaries of the existing cement. In other words, the second injection cement is often not clearly identified until it enters an area, as viewed using lateral projection fluoroscopy, that the first injection did not fill. Due to the difficulty of observing the flow of cement during the second injection, the risk of spinal cord compression, unwanted venous filling and/or related damage, is increased. In particular, it is a challenge to observe when the cement extends posteriorly towards the epidural venous plexus, a group of veins that lie anterior to the spinal cord. Over injection can lead to the filling of these veins with cement and result in paraplegia or severe nerve compression. Pulmonary embolism is also possible.

Some of the foregoing difficulties may be overcome using a biplane angiography, where it is possible to see the cement in two planes simultaneously. However, it is not possible to judge the depth by the anterior-posterior projection and does not overcome the issue of control on the lateral projection of the posterior extent of the degree of cement filling. Furthermore, the expense and rarity of biplane angiographic equipment can make this an inaccessible option of many patients.

SUMMARY OF THE INVENTION

It is therefore an object of the present invention to provide a novel method and apparatus for strengthening vertebral bodies which obviates or mitigates at least one of the disadvantages of the prior art.

In one aspect of the invention there is provided a kit for use in performing vertebroplasty comprising a first bone cement for strengthening a vertebral body, the first bone cement having a first imaging property and a second bone cement for strengthening the vertebral body having a second imaging property. When the vertebral body is exposed to an imaging device, an injection of the second bone cement is distinguishable from an injection of the first bone cement.

An apparatus and method for performing vertebroplasty are provided. In one embodiment of the invention, there is provided a kit for performing vertebroplasty having two packs, each pack having the necessary components for performing vertebroplasty via each pedicle of the damaged vertebrae. Each pack is sterilized, so that if the vertebroplasty performed via one pedicle is sufficient, then the second pack can be saved for later use. In another embodiment, each pack within the kit has two cements, each cement having different imaging properties, such that each cement will appear different when viewed with an imaging device in the lateral plane and/or will be viewable when overlapping. A presently preferred embodiment involves two packs having methylmethacrylate powder but each pack has a different amount of opacifier to be added to the powder, such that when each cement is mixed and injected, each cement is visible when exposed to X-ray lateral fluoroscopy. A method is also provided that utilizes the kit, and which allows a medical professional to monitor a second injection of cement via the second pedicle and thus reduce the risk of spinal cord compression due to unwanted flow of cement into the spinal cord, or nerve compression.

BRIEF DESCRIPTION OF THE DRAWINGS

The present invention will now be explained, by way of example only, with reference to certain embodiments and the attached Figures in which.

DETAILED DESCRIPTION OF THE INVENTION

Figure 1:
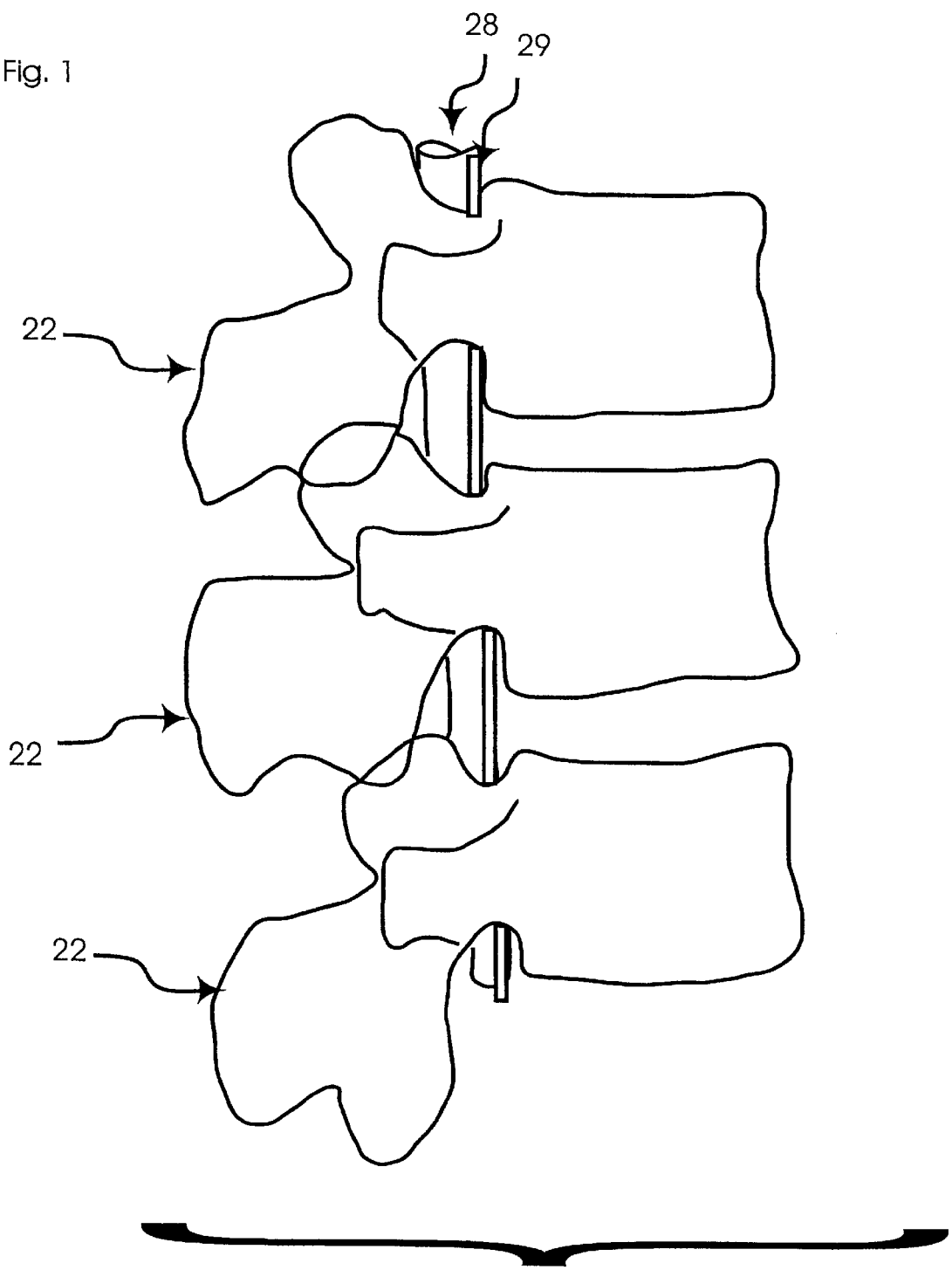
FIG. 1 is a lateral view of three normal vertebrae.
Figure 2:
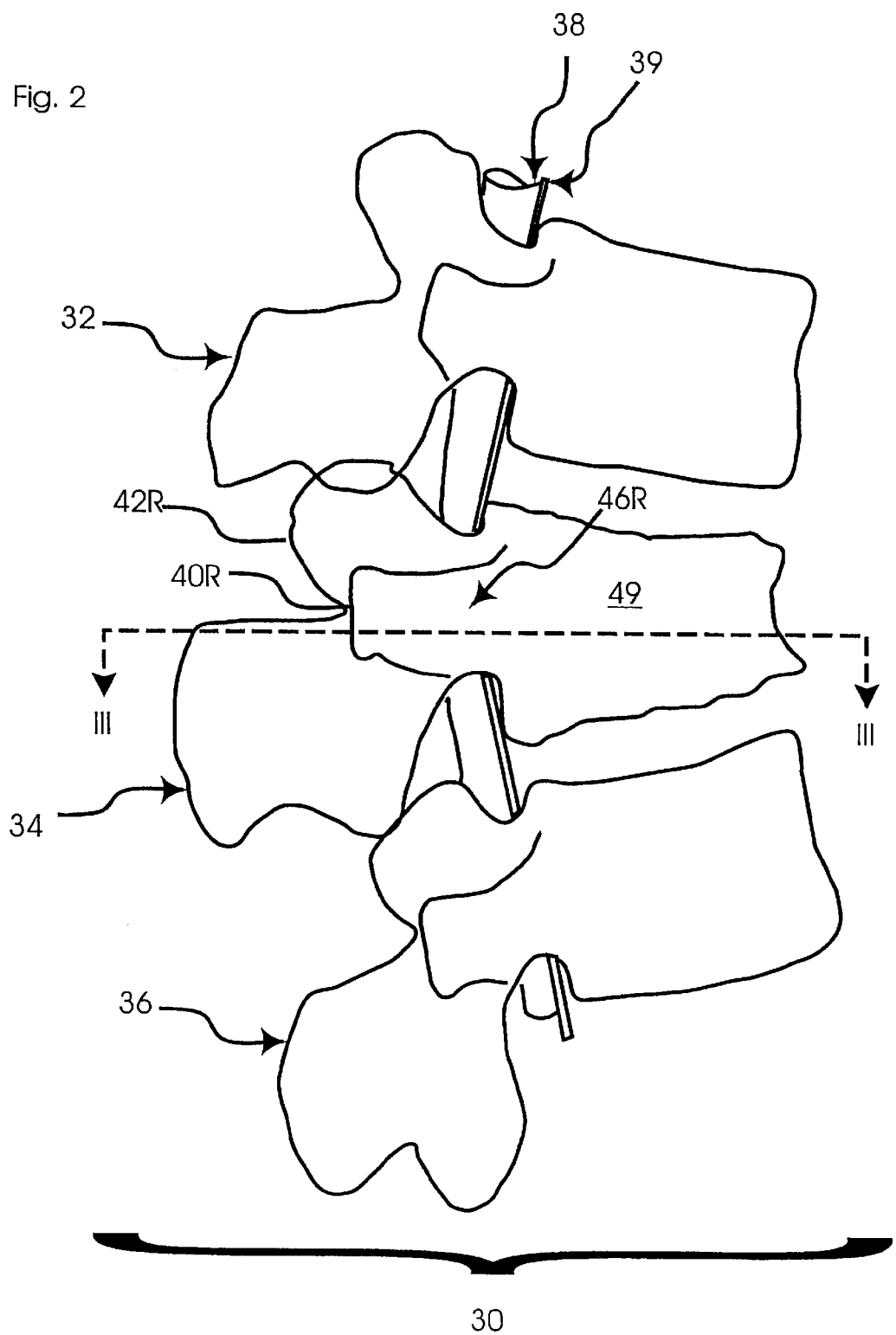
FIG. 2 is a lateral view of three vertebrae wherein the middle vertebral body has a condition suitable for treatment by vertebroplasty.

Before discussing embodiments of the present invention, various components of vertebrae and the spine will be discussed. FIG. 1 is a right lateral view of a segment 20 of a normal spine. Segment 20 includes three vertebrae 22. The spinal cord 28 and epidural veins 29 run through the spinal canal of each vertebrae 22. In contrast to segment 20 of FIG. 1, FIG. 2 shows a right lateral view of a segment 30 of a spine wherein at least one of the vertebra has a condition suitable for treatment by vertebroplasty. Segment 30 includes a first vertebra 32, a compressed middle vertebra 34 and a third vertebra 36. Spinal cord 38 and epidural veins 39 run through the spinal canal of each vertebra 32, 34 and 36.

Figure 3:
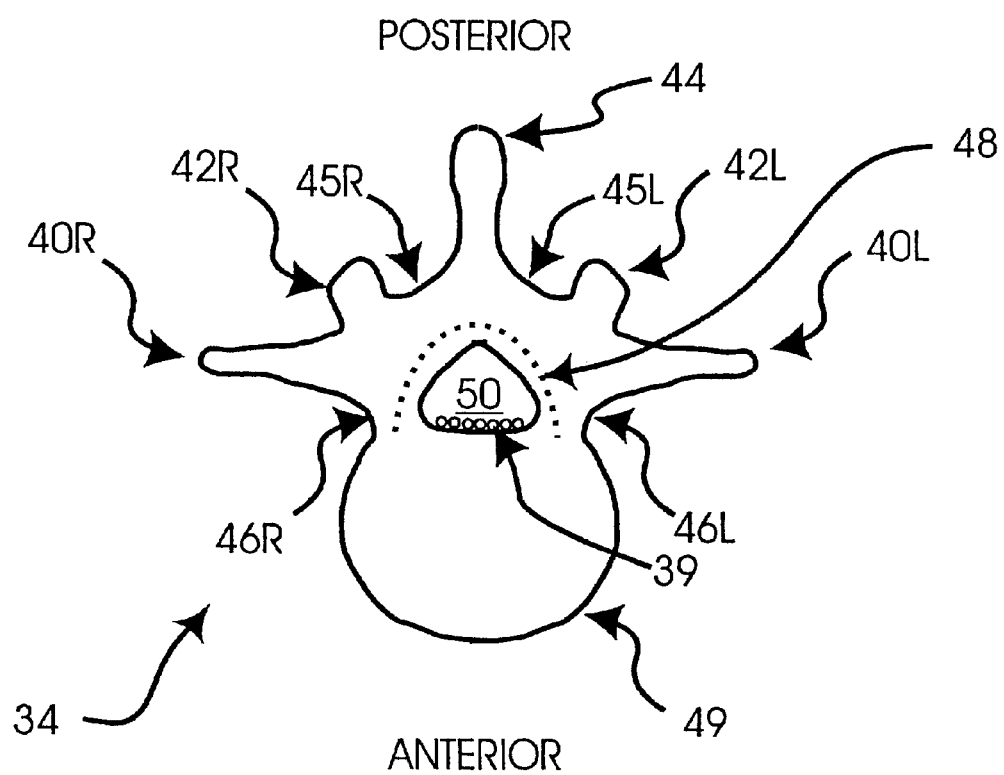
FIG. 3 is an axial view of the compressed vertebral body through line III—III of FIG. 2.

As shown in FIGS. 2 and 3, vertebra 34 has a right and left transverse process 40R, 40L, a right and left superior articular process 42R, 42L, and a spinous process 44 at the posterior of vertebra 34. Right and left lamina 45R, 45L lie intermediate spinous process 44 and superior articular processes 42R, 42L, respectively. Right and left pedicles 46R, 46L and lamina 45R, 45L cooperate to form the vertebral arch 48. The vertebral body 49 is located at the anterior of vertebra 34, and is joined to arch 48 at pedicles 46R, 46L. Arch 48 and vertebral body 49 define the spinal canal 50 through which spinal cord 38 passes. Epidural veins 39 lie between spinal cord 38 and vertebral body 48. As seen in FIG. 2 vertebral body 49 is compressed as a result of any condition suitable for treatment by vertebroplasty. Such conditions generally include benign osteoporotic fractures, malignant metastatic disease and benign tumours of the bone.

Figure 4:
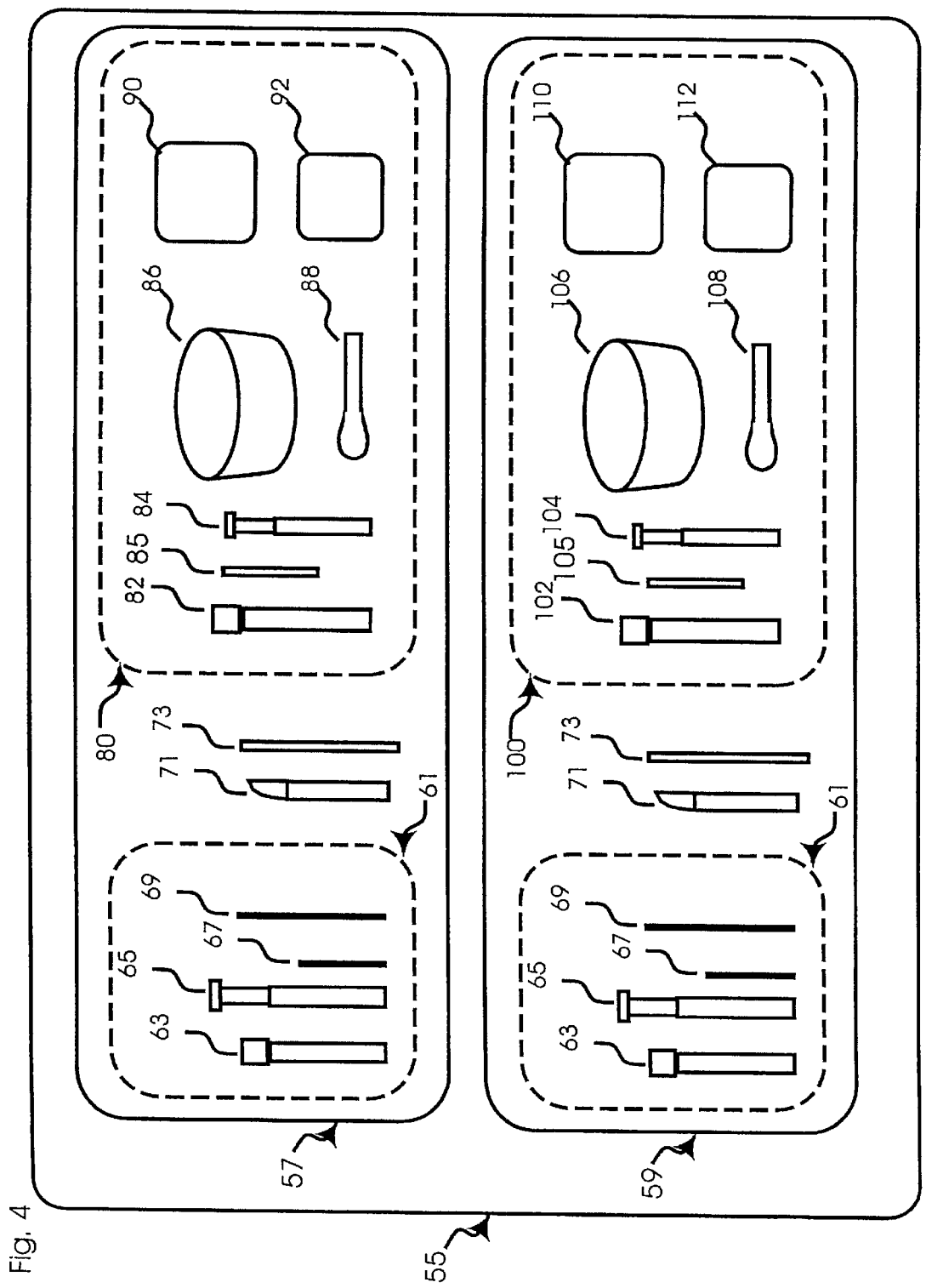
FIG. 4 is a schematic representation of a kit for vertebroplasty in accordance with an embodiment of the invention.

Referring now to FIG. 4, a kit, in accordance with an embodiment of the invention, for the strengthening of vertebral body 44 is indicated generally at 55. As will be understood by those of skill in the art, the individual items in FIG. 4 are known, and are drawn in a simplified form and kit 55 should not be construed as limited to the representation of FIG. 4. Kit 55 includes a first pack 57 and a second pack 59. Kit 55 and each pack 57, 59 therein are housed within a sterile packaging suitable for refrigeration and/or storage until use. Each pack 57, 59 has a local anaesthesia assembly 61, including a vial of local anaesthesia 63, a syringe 65 for administering the anaesthesia, a needle 67 for anaesthesia aspiration and a long needle 69 for anaesthesia injection. It is presently preferred that vial 63 has ten cubic-centimetres of 1% lidocaine without adrenaline, and accordingly that syringe 65 is a ten cc syringe. It is also presently preferred that needle 67 is sixteen gauge, while long needle 69 is twenty-two gauge. It will be understood that anaesthesia assembly 61 consists of well-known components, and that other components can be substituted, as desired.

Each pack 56, 59 also includes a scalpel 71 for making an incision to perform vertebroplasty. It is presently preferred that scalpel 71 is disposable and has a number-eleven blade. It will be understood that any scalpel or other functionally equivalent surgical tool suitable for vertebroplasty can be used, as will occur to those of skill in the art.

Packs 57, 59 also include at least one vertebroplasty needle 73. Where kit 55 is for use on a lumbar vertebral body, then it is generally preferred that an eleven gauge vertebroplasty needle 73 is included. Where kit 55 is for use on a thoracic vertebral body, then it is generally preferred that a thirteen gauge vertebroplasty needle 73 is included. It will be understood, however, that various sizes and combinations of vertebroplasty needles 73 can be included into each pack 57, 59 to offer greater flexibility for each kit 55, as desired and/or required for a particular vertebroplasty operation. One suitable vertebroplasty needle is the Cook needle, model DBBN-10(11)(13)-10.0(15.0)-m1(m2) from Cook, Inc., Bloomington Ind.

Pack 57 also includes the ingredients for a first bone cement for strengthening a vertebral body and which has a first imaging property. In a present embodiment, the ingredients and mixing devices for the first bone cement are provided in a first cement assembly 80. First cement assembly 80 includes monomer liquid 82 in a vial, a monomer compatible aspiration syringe 84, a monomer aspiration needle 85, a mixing bowl 86, a mixing spatula 88, a polymer powder 90, and a first opacifier 92.

It is believed that the vial of monomer liquid 82 should contain from about five cubic-centimetres to about twenty cubic-centimetres of monomer. Any monomer that is intended for use with a corresponding polymer powder 90 can be used. For example, in Osteobond there is a liquid component of 99.25% methylmethacrylate monomer, 0.75% N,N-dimethyl-p-toluidine and 75±10 ppm hydroquinone in Osteobond Copolymer Bone Cement from Zimmer Inc., 1800 West Center Street, Warsaw Ind. 46580. Other suitable monomer liquids are included in other bone cements as offered by the various bone cement suppliers. Preferably, the vial contains from about seven cubic-centimetres to about fifteen cubic-centimetres of monomer liquid 82. More preferably, the vial contains from about ten cubic-centimetres to about thirteen cubic-centimetres of monomer liquid 82. It is presently preferred, however, that the vial contains from about twelve cubic-centimetres of monomer liquid 82. Overall, it will be understood that any composition and/or quantity of monomer liquid 82 can be provided that allows a radiologist or other vertebroplasty professional to prepare polymer powder 90 with a desired consistency.

Monomer aspiration syringe 84 is accordingly sized to accommodate the volume of monomer liquid 82. Preferably, syringe 84 is DMSO (dimethylsulphoxide) compatible, which is designed so that the plunger does not swell when it contacts monomer liquid 82. A suitable source for syringe 84 is MTI, Micro Therapeutics Inc., 2 Goodyear, Irvine Calif. 92618.

A suitable mixing bowl 86 is a small disposable plastic bowl, such the "gent-l-kare" sterile one quart single-use disposable utility bowl made by Premium Plastics Inc., Chicago Ill. 60616. Both mixing bowl 86 and mixing spatula 88 are made from a material that is suitable for use in the mixing of the bone cement, as is known to those of skill in the art. Other suitable mixing devices, such as the closed mixing system known as the "vacuum cement mixing" device supplied by Howmedica can be used, as will occur to those of skill in the art.

Polymer powder 90 is packaged in any suitable sterile sachet. However, any bag or storage means can be used and which are suitable for holding from about five grams to about forty grams of methylmethacrylate. Preferably, polymer powder 90 is from about ten grams to about thirty grams of methylmethacrylate. More preferably, polymer powder 90 is from about twelve grams to about twenty grams of methylmethacrylate. It is presently preferred, however, that polymer powder 90 is about eighteen grams of methylmethacrylate.

It will now be apparent that the foregoing monomer liquid 82 and polymer powder 90 is obtainable in Osteobond. Other suitable bone cements include calcium carbonate, calcium phosphate, zirconium, or oxalate or hydroxyappatite derivatives, as will be understood by those of skill in the art.

First opacifier 92 is packaged in a sterile satchet or equivalent storage means. In the present embodiment, where polymer powder 90 is methylmethacrylate then first opacifier 92 is barium powder. It is believed that there should be a mass of barium of from about ten percent to about fifty percent of the mass of the methylmethacrylate. Preferably, there should be a mass of barium of from about fifteen percent to about forty-five percent of the mass of methylmethacrylate. More preferably, there should be a mass of barium powder of from about twenty percent to about forty percent of the mass of methylmethacrylate. It is presently preferred, however, that there should be a mass of barium of about one-third of the mass of methylmethacrylate, and thus, where there is eighteen grams of methylmethacrylate there should be about six grams of barium. In general, it will be understood that a sufficient amount of barium should be added to the first cement that provides a suitable radio-opacity without degrading the physical properties of the first cement. Other suitable opacifiers, such as calcium phosphate, calcium carbonate, tantalum, tungsten or zirconium can be used, as will occur to those of skill in the art.

Pack 59 includes the ingredients for a second bone cement for strengthening a vertebral body that is compatible and/or usable with the first bone cement and which has a second imaging property. In the present embodiment, the ingredients and mixing devices for the second bone cement are provided in a second cement assembly 100. Second cement assembly 100 includes monomer liquid 102 in a vial, a monomer aspiration syringe 104, a monomer aspiration needle 105 a mixing bowl 106, a mixing spatula 108, polymer powder 100, and a second opacifier 112.

It is presently preferred that monomer liquid 102, syringe 104, needle 105, bowl 106, spatula 108 and powder 110 are the same as liquid 82, syringe 84, bowl 86, spatula 88 and powder 90, respectively, from pack 57.

However, second opacifier 112 has a different composition and/or quantity from first opacifier 92, so that when it is mixed into a second bone cement the second bone cement has a different imaging property from the first bone cement. Second opacifier 112 is packaged in a bag, similar to first opacifier 92. In the present embodiment, second opacifier 112 is also barium but has a different, preferably higher, quantity that first opacifier 92. It is believed that there should be about fifteen percent to about three-hundred percent more barium in second opacifier 112 than first opacifier 92. Preferably, there should be about there should be about thirty percent to about two-hundred-and-fifty percent more barium in second opacifier 112 than first opacifier 92. More preferably, there should be about forty percent to about two-hundred percent more barium in second opacifier 112 than first opacifier 92. It is presently preferred, however, that there should be about one-hundred-and-eighty percent more barium powder in second opacifier 112 than first opacifier 92. Thus, in a presently preferred embodiment, there is about eleven grams of barium powder in second opacifier 112 to contrast the six grams of barium powder in first opacifier 92. In general, it will be understood that a sufficient amount of barium should be added to polymer powder 110 to provide a radio-opacity that differs from the radio-opacity of the first cement, but without degrading the physical properties of the second cement.

Figure 5:
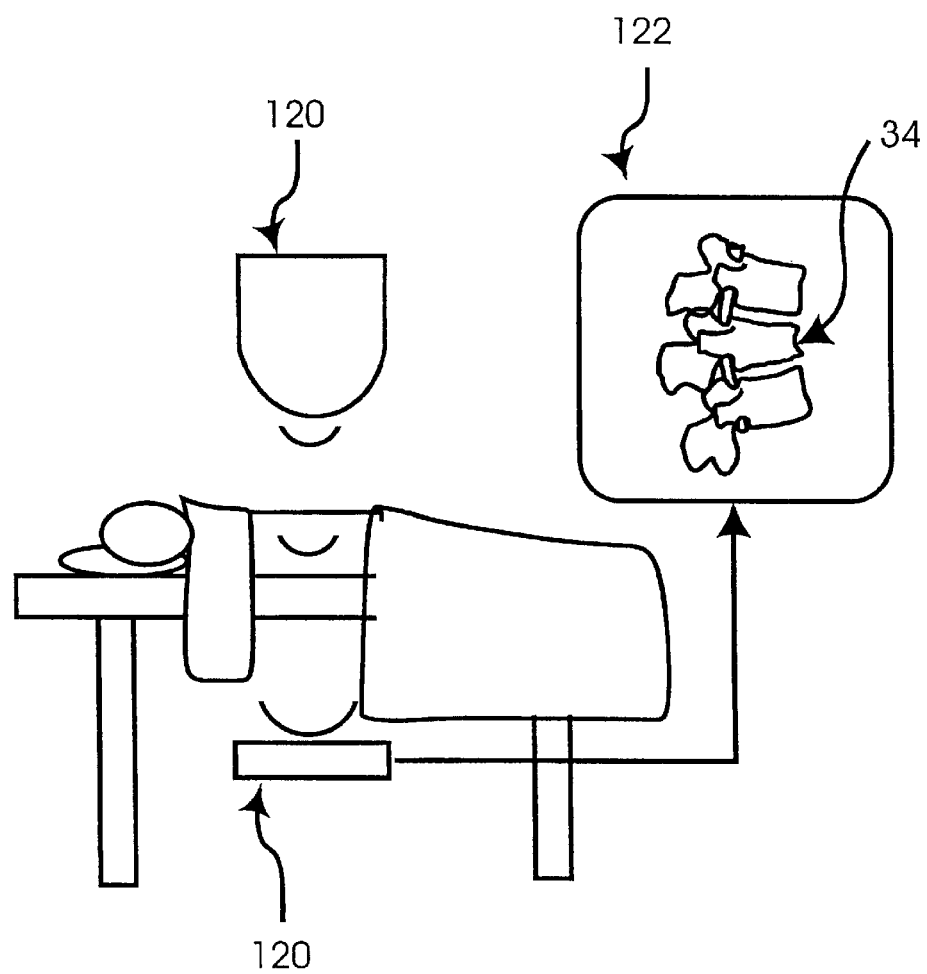
FIG. 5 is a schematic representation of an operating table and an imaging device for performing vertebroplasty, showing a patient lying prone and prepped for vertebroplasty and an imaging display showing the lateral view of FIG. 2.
Figure 6:
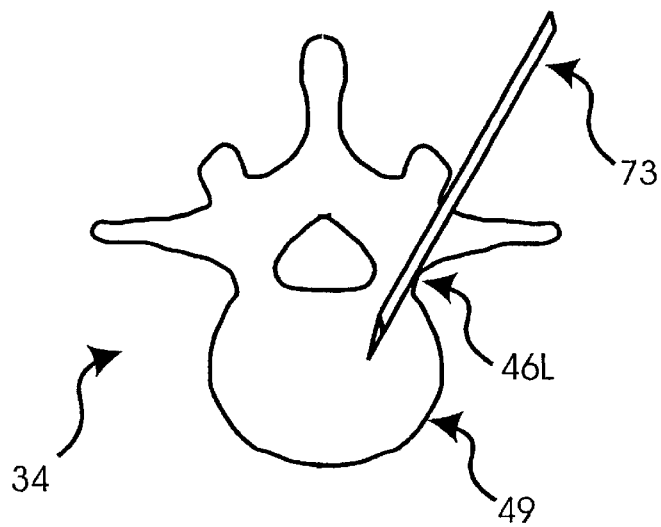
FIG. 6 is the axial view of FIG. 3 showing the insertion of a vertebroplasty needle through the left pedicle.
Figure 7:
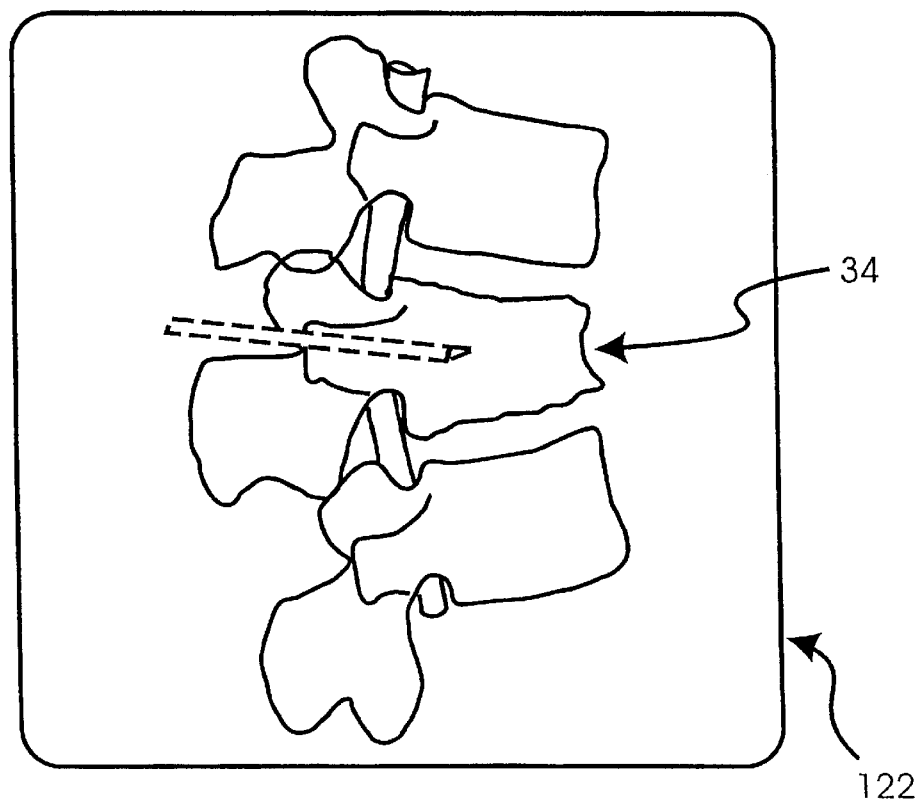
FIG. 7 is the lateral view of FIG. 6, as projected by the imaging device.

A method for performing vertebroplasty in accordance with an embodiment of the invention will now be discussed, utilizing kit 55 and performed on a patient having vertebrae 34. Referring now to FIG. 5, the patient is placed in the prone position so that vertebrae 34 is within the field of an imaging device 120, which in a present embodiment is an X-Ray projection fluoroscopy imaging device. Other imaging devices can be used, as will occur to those of skill in the art. When imaging device 120 is 'on', vertebrae 34 is projected onto display 122. For purposes of explaining the present embodiment, vertebrae 34 is projected onto display 122 from the same lateral view as shown in FIG. 2. The skin overlying vertebrae 34 is prepped and draped in the usual manner with sterile technique. Next, the seal on kit 55 is broken, and the seal on pack 57 is broken. Anaesthesia assembly 61 is opened and utilized so that anaesthesia 63 is injected into the skin underlying fat and into the periosteum of the pedicle to be entered. For purposed of explaining the present method, it will be assumed that left pedicle 46L will be entered first. Next, using scalpel 71, a skin incision of about five millimetres is made with scalpel 71. As shown in FIGS. 6 and 7, at this point vertebroplasty needle 73 is inserted into the incision and passed down left pedicle 46L, preferably until it enters the vertebral body and reaches the junction of the anterior and middle thirds.

Figure 8:
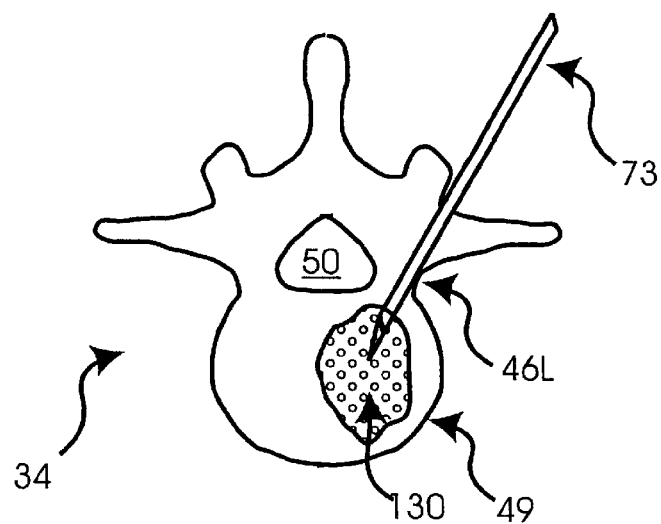
FIG. 8 is the axial view of FIG. 6 showing the injection of a first cement having a first imaging property into the vertebral body.
Figure 9:
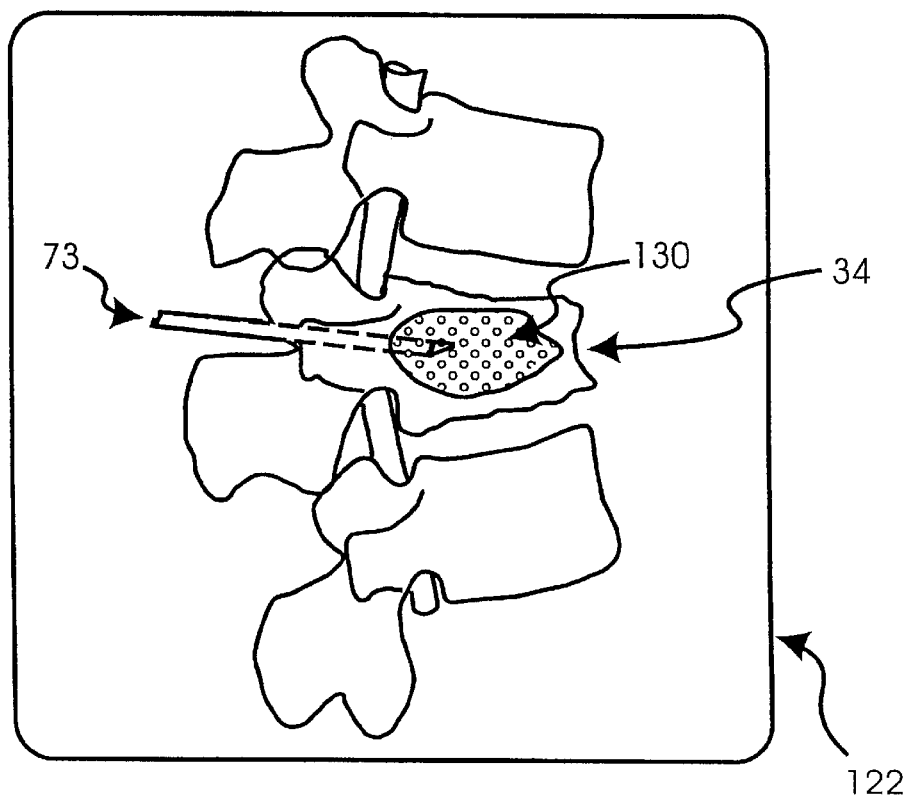
FIG. 9 is the lateral view of FIG. 8, as projected by the imaging device.

At this point, first cement assembly 80 is opened. Powder 90 and first opacifier 92 are placed in mixing bowl 86 and monomer 82 is injected into mixing bowl 86 using syringe 84. A first cement for strengthening a vertebral body and having a first imaging property is thus prepared by mixing the contents of mixing bowl 86 with spatula 88. In the present embodiment, the first imaging property is determined by the quantity of first opacifier 92 within the first cement. As shown in FIGS. 8 and 9, the first cement is injected into vertebral body 49 via left pedicle 46L through needle 73, the first cement being indicated at 130. Opacifier 92 allows first cement 130 to be detected by imaging device 120 and is thus viewable on display 122 as having a first imaging property. The first imaging property is represented in first cement 130 as a pattern of small circles. Accordingly, the quantity and flow-route of first cement 130 is monitored on display 122, as shown in FIG. 9.

At this point, a decision can be made as to whether a sufficient quantity of first cement 130 that has been injected. This decision is made using known criteria and is typically made by the radiologist, physician and other vertebroplasty professional who is performing the method. If it is determined that enough cement has been injected to provide the desired strength to vertebral body 34, then the treatment method is complete and the patient is prepared for removal from the X-ray room and transferred to the observation area. Pack 59 is still sterile and can be place back into refrigeration or storage for use on another patient at a later date.

Figure 10:
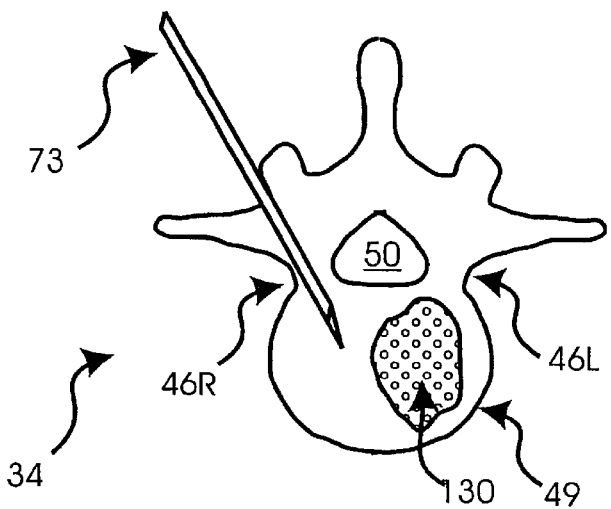
FIG. 10 is the axial view of FIG. 8 showing the insertion of a vertebroplasty needle through the right pedicle.
Figure 11:
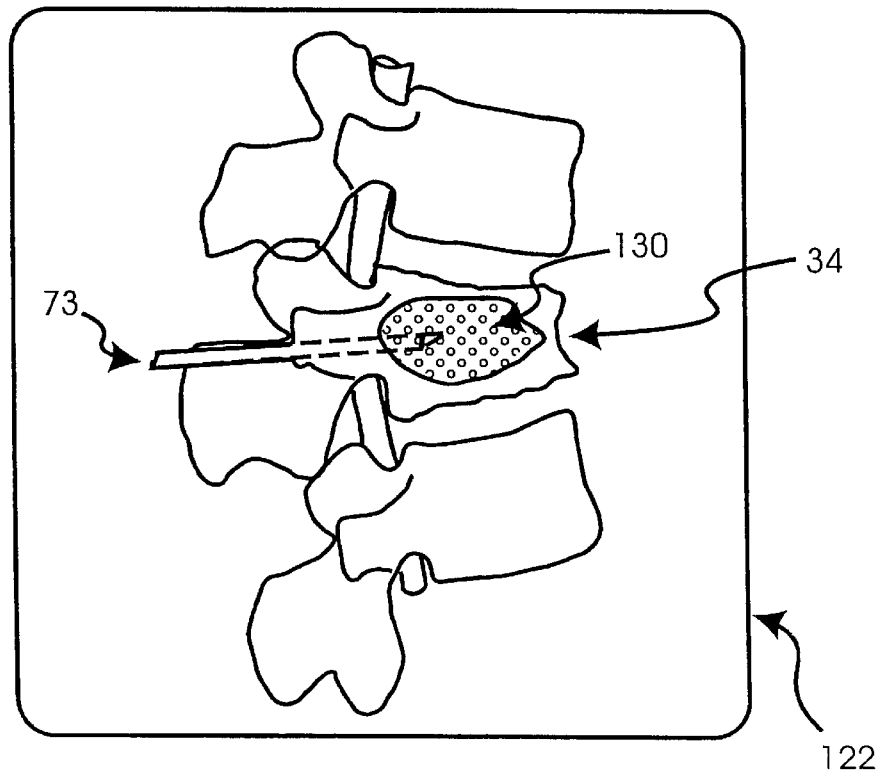
FIG. 11 is the lateral view of FIG. 10, as projected by the imaging device.

If, however, it is determined that another injection is required along right pedicle 46R, then pack 59 is opened and anaesthesia assembly 61 therein is opened and anaesthesia 63 is injected into the skin posterior to right pedicle 46R. Scalpel 71 of pack 59 is then used to make the appropriate incision, and vertebroplasty needle 73 of pack 59 is inserted into vertebral body 49 via right pedicle 46R, as shown in FIGS. 10 and 11.

Figure 12:
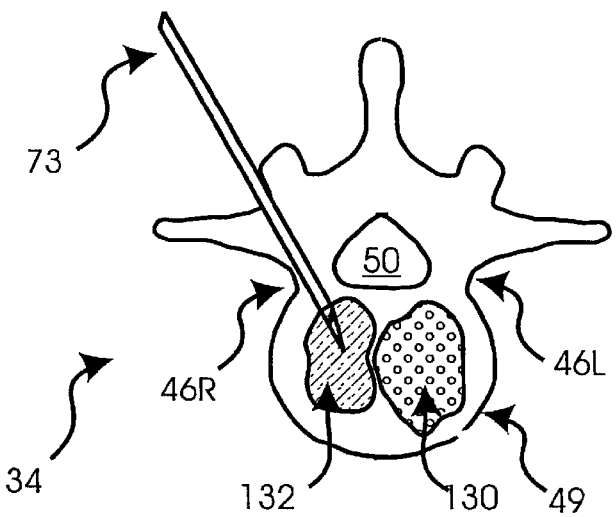
FIG. 12 is the axial view of FIG. 10 showing the injection of a second cement having a second imaging property into the vertebral body; and, FIG. 13 is the lateral view of FIG. 12, as projected by the imaging device.
Figure 13:
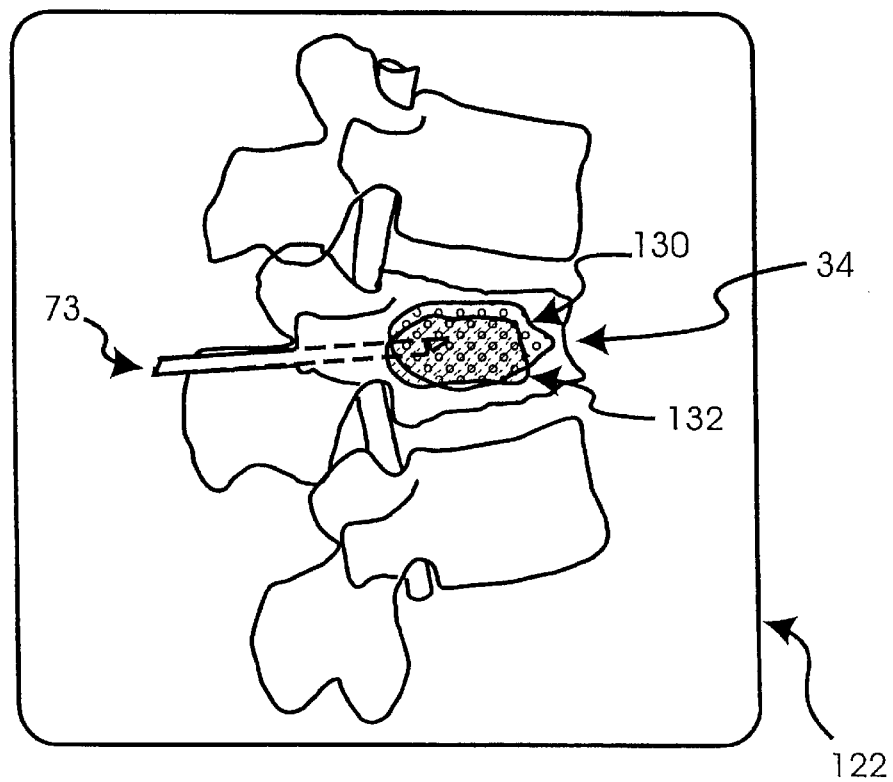

At this point, second cement assembly 100 is opened. Powder 110 and second opacifier 112 are placed in mixing bowl 106 and monomer 102 is aspirated into mixing bowl 106 using syringe 104. A second cement for strengthening a vertebral body that has a second imaging property, (which in the present embodiment has different radio-opacity), is thus prepared by mixing the contents of mixing bowl 106 with spatula 108. In the present embodiment, the second imaging property is determined by the quantity of second opacifier 112 within the second cement. As shown in FIGS. 12 and 13, the second cement is injected into vertebral body 49 via right pedicle 46R through needle 73, the second cement being indicated at 132. Opacifier 112 allows second cement 132 to be detected by imaging device 120 and is thus viewable on display 122 as having a second imaging property. The second imaging property is represented in second cement 132 as a pattern of diagonal lines. Accordingly, the quantity and flow-route of second cement 132 is monitored on display 122, as shown in FIG. 13. In particular, the quantity and flow-route of second cement 132 can be monitored in contrast to the first cement 130, due to the contrasting or different imaging properties of first cement 130 and second cement 132. By monitoring the flow-route of second cement 132, the injection of second cement 132 can be terminated before it reaches spinal canal 50 and thus reduce the likelihood of spinal cord compression and/or related damage. Once a sufficient amount of second cement 132 has been injected, the method is complete and the patient is prepared for discharge.

It should be understood that the opacifier in at least one of the first and second cements can be in the form of particles dispersed throughout the respective cement. In certain circumstances, the motion of such particles can increase the ability to detect cement motion and filling. For example, when using methylmethacrylate powder with barium, the barium can be in the form of powder and/or particles. It is presently preferred that the barium particles are about one millimetre in size, however, other particles sizes will occur to those of skill in the art. When used with an X-ray imaging system, other particles can include, for example, calcium phosphate, oxalate, zirconium, tantalum and/or tungsten. Other types of particles will occur to those of skill in the art.

It can be desired to use a first cement with a first density of radio-opaque particles, and a second cement having a second density of radio-opaque particles. Generally, it is preferred that the second cement injection has a greater density of particles than the first cement injection. Furthermore, previously discussed, it is generally preferred that the method is performed so that second cement injection appears in front of the first cement injection, as displayed on the imaging display.

It can be desired that only one of the cements has radio-opaque particles, while the other cement has a radio-opaque powder. While not necessary, it is generally preferred that the cement with the particles is used for the second injection of cement.

Other variations of how to provide two different opacifiers that will make each respective injection of each cement appear contrasting and/or different under an imaging system will occur to those of skill in the art, and are within the scope of the invention.

While the embodiments discussed herein are directed to particular implementations of the present invention, it will be apparent that the sub-sets and variations of these embodiments are within the scope of the invention. For example, kit 55 can include drapes, disinfectant and/or sponge tipped disinfectant applicators for use in the preparation of the patient prior to performing the operation. Other items of assistance during a vertebroplasty can be added to kit 55, as desired.

It is to be understood that the individual packs 57, 59 of kit 55 need not include anaesthesia assemblies, vertebroplasty needles, scalpels, etc. and that it is contemplated that each pack 57, 59 need only include a first cement for strengthening a vertebral body that has a first imaging property, and a second bone cement for strengthening a vertebral body that has a second imaging property, whereupon injection thereof each cement is visible by an imaging system, such as a X-ray or other radiographic imaging system. The other items in pack 57, 59 can be obtained and/or assembled from other sources prior to performing the method.

The ability to detect motion of cement during injection can be increased where radiopaque vertebroplasty needles are used, thus allowing the detection of motion of cement as the cement travels along the length of the needle.

It will be understood that each pack 57, 59 can be packaged and/or sold separately, and/or need not be included in an entire kit 55. Furthermore, kit 55 can be sold as having two of pack 59, two of pack 57, or, as previously discussed, one pack 57 and one pack 59. By offering different combinations of kit 57 and packs 57, 59 vertebroplasty professionals can be offered kits having cements with imaging properties that are personally preferred by the professional, and/or allow the purchase of additional individual packs that complement left-over individuals packs from procedures that only required the use of one pack.

It is contemplated that the first and second bone cements can also be bone cements that are bioactive, integratable, stimulate bone growth and/or are resorbable. Orthocomp™ cement by Orthovita of 45 Great Valley Partway, Malvern Pa. 19355 is one such cement. Other suppliers of such cements include Howmedica/Stryker of 6300 Sprinkle Road, Kalamazoo, Mich. 49001, and Codman/Depuy of 325 Paramount Drive Raynham Mass. 02767. It is contemplated that as other suitable cements are developed and/or approved, the contents of the kit can vary to suit the surgical procedure used to inject the first and second cements.

It is also contemplated that the mechanism for injecting the cement can be automatically controlled via a computer or other controller that receives the image from the imaging device and has an output connected to the vertebroplasty needle injection mechanism. Such a controller can be programmed to determine, based on the received image, when to commence, stop or otherwise control the flow of the injection of each cement.

While the present invention teaches first and second cements having differing densities and/or distributions of particles of barium to provide different imaging properties when exposed to lateral X-ray fluoroscopy, other opacifiers and/or imaging technologies can be used, as will occur to those of skill in the art. Other imaging technologies can include, for example, magnetic resonance imaging, and computed tomography.

It will be further understood that packs 57 and 59 within kit 55 can each have completely identical components, and, optionally kit 55 can further include a separate package of opacifier to be mixed with one of the cement assemblies to provide two different cements that will have different imaging properties. Alternatively, the extra opacifier need not be provided with kit 55, but can be obtained separately by a user of kit 55. The other permutations and combinations of kit 55 will now be apparent, and are within the scope of the invention.

It will also be understood that polymer powder 90 and first opacifier 92 can be premixed and packaged in a single sachet within first pack 57. Similarly, polymer powder 110 and second opacifier 112 can also be premixed.

While the present invention is generally suitable for known conditions that are treatable with vertebroplasty, it is contemplated that the present invention can be suitable for other conditions that require similar treatment. For example, prophylactic vertebroplasty can be performed in patients with critically low bone density.

The present invention provides a novel method and kit for increasing strength of vertebral bodies. In one embodiment, there is provided a first cement for strengthening a vertebral body which has a first imaging property, and a second bone cement for strengthening a vertebral body that is compatible with the first bone cement and which has a second imaging property, such that each cement is visible during injection under the guidance of an imaging system, such as lateral X-ray fluoroscopy. By providing these two cements, vertebroplasty can be performed by injection into both pedicles of the vertebra and allow a radiologist, physician or other vertebroplasty professional to observe the flow of the cements and thus more safely and/or effectively inject cement in the vertebral body and reduce the likelihood of spinal cord compression and/or related damage. The present invention also provides a kit for performing vertebroplasty, having a first pack for performing vertebroplasty through one pedicle, and a second pack for performing vertebroplasty through a second pedicle. Each pack can have a variety of different combinations, as desired. Each pack can be used independently. Unused packages can be stored for later use and a second conventional vertebroplasty procedure can be carried out using of the second pack.

I claim:

1. A kit for use in performing vertebroplasty comprising:
    a first bone cement for strengthening a vertebral body, said first bone cement having a first imaging property; and
    a second bone cement for strengthening said vertebral body having a second imaging property, such that when said vertebral body is exposed to an imaging device, an injection of said second bone cement is distinguishable from an injection of said first cement.

2. The kit according to claim 1 further comprising at least one local anaesthesia.

3. The kit according to claim 1 further comprising at least one vertebroplasty needle.

4. The kit according to claim 1 further comprising at least one scalpel.

5. The kit according to claim 1 wherein at least one of said first bone cement and said second bone cement comprises a polymer and an opacifier.

6. The kit according to claim 5 wherein said polymer is methylmethacrylate.

7. The kit according to claim 5 wherein said opacifier is barium.

8. The kit according to claim 7 wherein said first and second bone cements comprise first and second polymers and first and second opacifiers, respectively, and wherein said first polymer and said second polymer is methylmethacrylate and said second opacifier has from about fifteen percent to about three-hundred percent more barium than said first opacifier.

9. The kid according to claim 7 wherein said first and second bone cements comprise first and second polymers and first and second opacifiers, respectively, and wherein said first polymer and said second polymer is methylmethacrylate and said second opacifier has from about thirty percent to about two-hundred-and-fifty percent more barium than said first opacifier.

10. The kit according to claim 7 wherein said first and second bone cements comprise first and second polymers and first and second opacifiers, respectively, and wherein said first polymer and said second polymer is methylmethacrylate and said second opacifier has from about forty percent to about two-hundred percent more barium than said first opacifier.

11. The kit according to claim 1 wherein said first bone cement comprises a polymer and with a first opacifier and said second bone cement comprises a polymer and a second opacifier.

12. The kit according to claim 11 wherein said polymer in each of said first bone cement and said second bone cement is from about five grams to about forty grams of methylmethacrylate.

13. The kit according to claim 11 wherein said polymer in each of said first bone cement and said second bone cement is from about ten grams to about thirty grams of methylmethacrylate.

14. The kit according to claim 11 wherein said polymer in each of said first bone cement and said second bone cement is from about twelve grams to about twenty-five grams of methylmethacrylate.

15. The kit according to claim 11 wherein said polymer in each of said first bone cement and said second bone cement is about eighteen grams of methylmethacrylate.

16. The kit according to claim 15 wherein said first opacifier is about six grams of barium and said second opacifier is about eleven grams of barium.

17. The kit according to claim 11 wherein at least one of said first opacifier and second opacifier is a plurality of particles.

18. A method for performing vertebroplasty on a vertebral body comprising the steps of:

displaying said vertebral body on an imaging system;

performing a first injection of a first bone cement having a first imaging property into said vertebral body;

terminating said first injection when a desired amount of said fist bone cement fills said vertebral body, said desired level being determinable by viewing said imaging system;

performing a second injection of a second bone cement having a second imaging property into said vertebral body, said second imaging property being different from said first imaging property such that each of said first bone cement and said second bone cement are distinguishable on said imaging system; and terminating said second injection when a desired amount of said second bone cement fills said vertebral body, said desired level being determinable by viewing said imaging system.

19. The method according to claim 18 wherein said imaging system is an X-ray lateral fluoroscopy system.

20. The method according to claim 18 wherein said first bone cement comprises a polymer and with a first opacifier and said second bone cement comprises a polymer and a second opacifier.

* * * * *